United States Patent

Rupieper et al.

[11] Patent Number: 5,991,042
[45] Date of Patent: Nov. 23, 1999

[54] METHOD AND AN APPARATUS FOR THE CHARACTERISATION OF LACQUERED SURFACES

[75] Inventors: Paul Rupieper; Michael Höffer; Joachim Cramm, all of Wuppertal; Joachim Blum, Remscheid, all of Germany

[73] Assignee: Herberts GmbH, Wuppertal, Germany

[21] Appl. No.: 08/860,384

[22] PCT Filed: Feb. 7, 1997

[86] PCT No.: PCT/EP97/00555

§ 371 Date: Dec. 19, 1997

§ 102(e) Date: Dec. 19, 1997

[87] PCT Pub. No.: WO97/30342

PCT Pub. Date: Aug. 21, 1997

[30] Foreign Application Priority Data

Feb. 15, 1996 [DE] Germany ............... 196 05 520
Mar. 21, 1996 [DE] Germany ............... 196 11 062

[51] Int. Cl.⁶ .............. G01B 11/06; B05C 11/02
[52] U.S. Cl. .............. 356/381; 118/712; 356/446
[58] Field of Search .................. 356/381, 446; 118/712, 713; 427/10

[56] References Cited

U.S. PATENT DOCUMENTS

| | | |
|---|---|---|
| 3,916,168 | 10/1975 | McCarthy . |
| 4,977,853 | 12/1990 | Falcoff et al. .............. 118/665 |
| 5,062,298 | 11/1991 | Falcoff et al. .............. 73/597 |
| 5,208,766 | 5/1993 | Chang et al. .............. 364/552 |
| 5,229,835 | 7/1993 | Reinsch .............. 356/371 |
| 5,504,695 | 4/1996 | Yoshida et al. .............. 364/563 |
| 5,550,632 | 8/1996 | Harata .............. 356/446 |

FOREIGN PATENT DOCUMENTS

| | | |
|---|---|---|
| 350891 | of 0000 | European Pat. Off. . |
| 0 336 029 | 10/1989 | European Pat. Off. . |
| 0 350 891 | 1/1990 | European Pat. Off. . |
| 41 27 215 A1 | 2/1993 | Germany . |
| 42 27 817 A1 | 2/1994 | Germany . |

OTHER PUBLICATIONS

Scheibe et al., "Flexibles Prüfsystem für die Oberflächentechnik", pp. 287–299.

Garmsen, "Uber die Pürfung von Lackfarben an Keilförmlgen Schichten", *Farbe Und Lack*, 60 (1954), pp. 257–261.

Unterforsthuber, "Pigmente, Fullstoffe und Farbstoffe Für die Lackindustrie", *Technische Akademie Esslingen*, 1993, pp. 1–48.

*Primary Examiner*—Robert H. Kim
*Assistant Examiner*—Zandia V. Smith
*Attorney, Agent, or Firm*—Pillsbury Madison & Sutro LLP

[57] ABSTRACT

A method of determining the visual effect of lacquer coatings in which one, two or more lacquer coatings are applied to the surface of a flat substrate and are dried or hardened, wherein one or two of the lacquer coats are applied with a coat thickness gradient, and one or more surface properties which influence the visual impression are subsequently each measured on the lacquered surface thus obtained, at measuring points distributed over the surface, by means of one or more optical methods of measurement, and the respective thickness of the lacquer coat(s) applied in the form of a gradient is also measured, as well as an apparatus for carrying out the method.

24 Claims, 2 Drawing Sheets

METHOD AND AN APPARATUS FOR THE CHARACTERISATION OF LACQUERED SURFACES

FIELD OF THE INVENTION

This invention relates to a method and to an apparatus for the characterisation of lacquered or multi-layer coated surfaces as regards their visual effect.

BACKGROUND OF THE INVENTION

The visual effect of a lacquered or multi-layer coated surface results from the interplay of various optical impressions, such as gloss and structure, and such as colour shade, which in turn is composed of colour location, brightness and colour intensity, for example. In the case of multi-layer coatings, the visual impression generally originates not only from the outer lacquer coat, but may also be influenced by one or more lacquer coats situated underneath. There is a wealth of methods which are known for the characterisation of a lacquered surface and which are suitable for describing the visual effect thereof on the eye of an observer. Examples include methods, which are known to one skilled in the art and which operate based on optical principles, of gloss measurement, of measuring gloss fogging (haze), of measuring colour shade (colorimetry) and of determining surface structures. One important influencing variable as regards the visual effect of a lacquered surface is the coat thickness at which the respective lacquer coat or respective lacquer coats have been applied. If a surface which is provided with a single-layer coating or a multi-layer coating is to be characterised as regards its visual effect as a function of the coat thickness of a specific lacquer coat or of the coat thickness of lacquer coats of particular interest, it is necessary to lacquer and measure a multiplicity of test panels. This multiplicity results firstly from the necessity of having to lacquer a plurality of test panels at different coat thicknesses, and secondly in order to obtain a statistical mean, which first ensures reproducibility of the readings obtained. The meaningfulness of readings obtained in this manner must nevertheless be considered critically, since a correlation with the visual impression is only obtained to a limited extent.

SUMARY OF THE INVENTION

The human eye has a function which perceives the visual impression of a lacquered area as an integral.

The object was to provide an efficient method of characterising lacquered surfaces as regards their visual effect as a function of the coat thickness of one or more lacquer coats. The method to be found should be reproducible, should provide measured results which correlate well with the integrating function of the human eye, and should make the dependence on coat thickness as perceptible as possible. It should be possible to carry out the method with the lowest possible consumption of lacquer and test panels, and the method should be capable of being used in the fields of lacquer development, quality control in lacquer manufacture, and in both the development and monitoring of lacquering processes, comprising both the application and the drying process.

It has been shown that this object is achieved by the method, to which the present invention firstly relates, for the determination of the visual effect of lacquer coatings, which is characterised in that one, two or more lacquer coatings are applied to the surface of a flat substrate and are dried or hardened, wherein one or two of the lacquer coats are applied with a coat thickness gradient, and one or more surface properties which influence the visual impression are subsequently each measured on the lacquered surface thus obtained, at measuring points distributed over the surface, by means of one or more optical methods of measurement, and the respective thickness of the lacquer coat applied in the form of a gradient or the respective thickness of each one of the two lacquer coats applied in the form of a gradient is also measured.

If two lacquer coats have a coat thickness gradient in the method according to the invention, the two lacquer coats are preferably applied with coat thickness gradients disposed at right angles to each other.

The measurements are preferably made with the aid of measuring points which are distributed in the form of a grid-like pattern over the whole area of the lacquer coating.

It is also possible to make the measurements on one partial area of interest only of the lacquered surface, wherein the measuring points are preferably disposed in the form of a grid-shaped pattern in this embodiment also.

Test panels are preferably used as the substrate with a flat surface. This expression is used in the following text without constituting a limitation, however.

In particular, the method according to the invention enables the optical data points obtained to be plotted on one or more correlation diagrams for the associated thickness of one wedge-shaped coat or of the two wedge-shaped coats. In the case of two lacquer coats which are applied in the form of a gradient, for example, the data points can be plotted on a correlation diagram as a three-dimensional representation (a spatial representation of all the optical data points as a function of the two coat thicknesses), or preferably in the form of a family of correlation diagrams (a plurality of representations comprising the corresponding subset of optical data points as a function of the coat thickness of one lacquer coat at a constant coat thickness of the second lacquer coat each time, or vice versa).

The method according to the invention is subject to no restrictions as regards the type of lacquers or lacquer coats. Thus the surfaces to be characterised may be single- or multi-layer coatings, which are produced using pigment-containing or pigment-free coating media. Examples include clear lacquers, colour- and/or effect-imparting base lacquers, covering lacquers and primer surfacer lacquers. Solvent-free, solvent-containing or aqueous liquid lacquers or powder coatings can be used for the production of the lacquer coats. The coating media may be single- or multi-component lacquers, and physically drying or chemically crosslinking (hardening) systems may be used. In chemically crosslinking systems, crosslinking can be induced thermally or by high-energy radiation. In connection with the present invention, the term "lacquer drying" can mean the physical drying or chemical crosslinking of a lacquer coat at ambient or elevated temperature, for example by stoving or by the effect of thermal radiation (IR radiation), or also by high-energy radiation, for example chemical crosslinking induced by UV radiation or by an electron beam.

If the surface of a single-layer coating is to be characterised, the lacquer in question is applied with a coat thickness gradient, namely in the form of a wedge, preferably by means of spray application, and is dried. The coat thickness gradient may cover a wide range, for example a range between greater than 0 and 100 $\mu$m. Application and/or subsequent drying can be effected so that the test panel is situated in a horizontal position during this procedure. Preferably, however, application or drying, most preferably application and drying, particularly of the lacquer coat which is applied in the form of a wedge, are effected on a test panel which is aligned outside the horizontal, and which is most preferably aligned vertically. In this respect, the region of greatest coat thickness of the lacquer coat applied in the form of a wedge is preferably situated at the lower end, i.e. at the end nearer the ground.

In the case of multi-layer coatings, one lacquer coat of which is applied in the form of a gradient, for example the base lacquer/clear lacquer double-layer coatings, particularly the base lacquer/clear lacquer double-layer effect coatings, which are known in the field of motor vehicle coatings, the same statements which have already been made in the preceding paragraph are applicable in principle, wherein one of the lacquer coats forming the multi-layer coating is applied with a coat thickness gradient. For example, the colour- and/or effect-imparting base lacquer coat or the clear lacquer coat of a base lacquer/clear lacquer double-layer coating can be applied with a coat thickness gradient.

If two lacquer coats have a coat thickness gradient, the two relevant lacquer coats of a multi-layer coating are preferably applied with coat thickness gradients which are disposed at right angles to each other, and are therefore each applied in the form of a wedge, preferably by means of spray application, and dried. The two coat thickness gradients may cover a wide range here, for example a range between 0 and 100 $\mu$m. Application and/or subsequent drying can be effected so that the test panel is situated in a horizontal position during this procedure. Preferably, however, application or drying, most preferably application and drying, particularly of the two lacquer coats which are applied in the form of a wedge, are effected on a test panel which is aligned outside the horizontal, and which is most preferably aligned vertically. In this respect, the region of greatest coat thickness of the lacquer coats applied in the form of a wedge is preferably situated at the lower end, i.e. at the end nearer the ground. It may be advantageous for this purpose, for example, to aerate the first lacquer coat applied in the form of a wedge, after the application thereof, on a test panel situated in a vertical position (in the case of the preferred wet-into-wet application), to dry it or harden it and then to apply the second wedge-shaped coat after rotation by 90°.

It should be mentioned that within the context of the present invention the term "test panel" does not constitute any restriction as regards the selection of material. Rather, the substrate is simply a smooth substrate which is flat or which is not curved, and which is rectangular for example, and is preferably made of any suitable materials, preferably of metal or plastics. Substrates which are particularly suitable are the rectangular test panels which are customary in the lacquer industry, and which may be of arbitrary dimensions, for example of the order of 300 mm×600 mm, or 600 mm×600 mm. These can be made of steel, for example. To ensure reproducibility, application is preferably effected by means of a customary automatic machine, such as that which is known from EP-B-0 350 891 for example. The coat thickness gradient or the two coat thickness gradients are preferably produced, for example, so that one or both lacquer coats in question are applied in a plurality of spray cycles, for example in two or more spray cycles, with the spray zones only partially overlapping.

In the method according to the invention, it is arbitrary which coat or coats are applied in the form of a wedge (in the form of a gradient). The coat or the two coats which are applied in the form of a wedge are advisedly those for which their effect on the overall visual impression is of interest. If two lacquer coats which are applied in the form of a wedge, these are preferably directly adjacent coats, which are preferably each applied as wedges disposed at right angles to each other.

For example, both the colour- and/or effect-imparting base lacquer coat and the clear lacquer coat of a base lacquer/clear lacquer double-layer coating, such as that which is known in the field of the mass-production coating of motor vehicles, can be applied with coat thickness gradients disposed at right angles to each other.

On the application of the coat of interest in the form of a gradient or of the two coats of interest in the form of gradients in the method according to the invention, one, two or more zones on the test panel are preferably left out. These zones may be strip-shaped for example, and may be formed at the edges of the test panel. This can be accomplished, for example, in that on the application of the coat in the form of a gradient or of each one of the two coats in the form of gradients the zones which are left out are separated by means of adhesives, for example by strip-shaped adhesive tapes. The remaining coats, including the further coat which is possibly applied in the form of a gradient, are applied in these zones in the same manner as on the test panel as a whole. In practice, the adhesive strips can be removed before the application of the further coat or coats, for example. In this manner, an additive determination can be made of the coat thickness of the coat applied in the form of a gradient or of the individual coats applied in the form of gradients at the individual measuring points, by comparison with the zones which are left out.

The method according to the invention is preferably conducted so that after careful calibration of the measuring system the relevant surface property which influences the visual impression of the test panel which is provided with the lacquer coating is measured n times, by means of optical methods of measurement, in the form of a grid which extends over the entire surface and which consists of n measuring points, wherein the dry coat thickness of the wedge-shaped lacquer coat concerned or the dry coat thicknesses of the wedge-shaped lacquer coats concerned are also measured for each measuring point. The number of measuring points n preferably equals about 400 to about 1000 or, if there are two wedge-shaped lacquer coats, n equals about 1500 to about 3000. The coat thickness is determined by customary methods known to one skilled in the art, such as magnetic or magnetic induction methods of measuring coat thicknesses (for example, such as those described by H. Kittel in Lehrbuch der Lacke und Beschichtungen, Volume 8/1, Verlag W. A. Colomb, 1980, page 140 et seq., and in the Glasurit-Handbuch Lacke und Farben, Curt R Vincentz Verlag, Munich, 1984, page 292 et seq.). On the preferred test panels made of steel, the coat thickness is preferably determined by magnetic induction methods of measurement. For example, the procedure employed in the method according to the invention preferably comprises making a plurality of measurements along a line of equal coat thickness of the lacquer coat concerned or of one of the lacquer coats concerned. Measurements can be made, for example, staring at a low coat thickness and progressing to the greatest coat thickness, preferably along equidistant lines in each case. Each individual line thereby covers identical coat thicknesses of the lacquer coat concerned or of one of the lacquer coats concerned. The different equidistantly disposed lines are associated with different coat thicknesses of the lacquer coat concerned or of one of the lacquer coats concerned. For example, a measuring grid is covered which comprises a total of about 400 to about 1000 measured values per test panel specimen. If there are 500 measuring points, for example, 25 readings can be taken along each of 20 different lines of equal coat thickness, or in the case of two wedge-shaped lacquer coats, for example, a measuring grid comprising a total of about 1500 to about 3000 measuring points is covered for each test panel specimen. If there are 1600 measuring points, for example, 40 readings can be taken along each of 40 different lines of equal coat thickness of one of the lacquer coats concerned. The spacings and number of the lines are preferably such that at least about one measuring point per square centimeter of lacquer surface is measured.

For their assessment, the readings obtained can be plotted as the ordinate and the coat thickness can be plotted as the abscissa of a correlation diagram. An unmistakeable pattern of n points, which is comparable with a fingerprint, it obtained for the property of the lacquered surface which is to be characterised. The possibility of assessing the visual properties of a lacquer coating is thus achieved. In particular, an assessment can be made of whether and how the visual properties depend on defined application and drying conditions and on a defined composition of one or more lacquers which are used for lacquering. In the case of two wedge-shaped lacquer coats, the readings obtained can be also represented for assessment as a correlation diagram in three-dimensional representation (a spatial representation of all the optical data points as a function of the two coat thicknesses), or preferably in the form of a family of correlation diagrams (a plurality of representations comprising the corresponding subset of the optical data points as a function of the coat thickness of one lacquer coat at a constant coat thickness of the second lacquer coat in each case, or vice versa). For example, the optical readings obtained can be plotted on the Z axis, and the associated coat thicknesses can be plotted on the X or Y axis of a three-dimensional correlation diagram, or the optical readings are plotted as the ordinate and the associated coat thicknesses of one of the wedge-shaped lacquered coats are plotted as the abscissa of a correlation diagram, wherein this is effected repeatedly for different coat thicknesses, each of which is constant, of the second wedge-shaped lacquer coat, or vice versa. A (three-dimensional) or a plurality of (two dimensional) unmistakeable patterns comprising a total of n points is obtained for the property of the multi-layer coated surface which is to be characterised, each of which patterns is comparable with a fingerprint. In particular, an assessment can be made of whether and how the visual properties depend on defined application and drying conditions and on a defined composition of the lacquers used for the production of the multi-layer coating.

The visually detectable properties of a single- or multi-layer coated surface are influenced by the complex interplay between a wealth of variable parameters of the lacquer materials themselves, of the actual application and of the lacquer drying process. For example, this interplay influences the occurrence and extent of phenomena which are perceptible to the eye, such as colour shade, brightness- and or colour flop (optical anisotropy), flow, run-off tendency, orange peel formation, microstructure, spray mist absorption capacity, etching effects, fogging of effect lacquers, hiding power, gloss and haze. These are phenomena which are ultimately reflected in the visual impression of a single- or multi-layer coated surface. Each of these properties can form the basis for the measurements to be made in the method according to the invention.

The aforementioned spray mist absorption capacity is manifested in particular when the individual gradient concerned is built up in the form of a plurality of lacquer coats which are applied additively. At the interface between two lacquer coats, the spray mist which arises on the application of the upper coat is absorbed by the coat underneath. The spray mist absorption capacity of lacquer coatings can be assessed in this manner; this is important, since spray mist in spray booths can scarcely be avoided in practice.

Examples of properties which can be determined and measured visually include gloss, gloss fogging (haze), surface structure comprising long- and short wave proportions, and colour shade, for example colour location, colour intensity and brightness.

Examples of procedures which can be used within the scope of the method according to the invention for measuring the gloss of lacquered surfaces include the customary goniophotometric methods based on the principle of luminous reflectance which are known to one skilled in the art, such as those described, for example, by H. Kittel in Lehrbuch der Lacke und Beschichtungen, Volume 8/1, Verlag W. A. Colomb, 1980, page 240 et seq., in the Glasurit-Handbuch Lacke und Farben, Curt R Vincentz Verlag, Munich, 1984, page 239 et seq., and in DIN 67530. The gloss measuring instruments which are preferably used within the scope of the method according to the invention are commercially available instruments, such as the Microgloss® and Micro-Tri-Gloss® instruments sold by the BYK-Gardner company for example.

Examples of procedures for measuring the gloss fogging (haze) of lacquered surfaces which can be used within the scope of the method according to the invention include the customary goniophotometric methods, which are likewise based on the principle of luminous reflectance and are known to one skilled in the art (such as those described, for example, in the Glasurit-Handbuch Lacke und Farben, Curt R. Vincentz Verlag, Munich, 1984, page 240). Commercially available instruments familiar to one skilled in the art can be used. One measuring instrument which is preferably used within the scope of the method according to the invention for determining haze is the Microhaze® instrument sold by the BYK-Gardner company for example.

Examples of colorimetric methods for lacquered surfaces which can be used within the scope of the method according to the invention include the customary methods, known to one skilled in the art, of determining the reflection curves of light, from which the colorimetric quantities $L^*$, $a^*$ and $b^*$ which are customary in the CIELAB system (as described, for example, by H. Kittel in Lehrbuch der Lacke und Beschichtungen, Volume 8/1, Verlag W. A. Colomb, 1980, page 252 et seq., and in the Glasurit-Handbuch Lacke und Farben, Curt R. Vincentz Verlag, Munich, 1984, page 220 et seq). All the customary measuring instruments familiar to one skilled in the art can be used. A colorimetric measuring instrument which is preferably used within the scope of the method according to the invention is the X-Rite MA 58 instrument sold by the X-Rite company. A measuring instrument which is preferably used for determining brightness is the Micrometallic® instrument sold by the BYK-Gardner company, for example.

An example of a method of determining the long wave and short wave proportion of the surface structure of lacquered surfaces which can be used within the scope of the method according to the invention is the goniophotometric method based on the principle of luminous reflectance modulated by surface structures, which is known to one skilled in the art. All customary measuring instruments familiar to one skilled in the art can be used. For example, the Wave-scan® instrument sold by the BYK-Gardner company is preferably used in the method according to the invention (see European Coatings Journal No. 1-2 (1995), pages 32–35).

In the method according to the invention, it is preferable to make measurements which give different measured results depending on the angle of illumination and/or observation on test panels which, during the application and/or drying of lacquer, preferably on the application and drying in particular of the lacquer coat which is applied in the form of a wedge or of the two lacquer coats which are applied in the form of wedges, were situated outside the horizontal position, and were preferably situated in a vertical position. It is particularly preferred that the region of greatest coat thickness of the lacquer coat which is applied as a wedge, or of the two lacquer coats which are each applied as wedges and which are preferably disposed at right angles to each other, were each situated at the lower end of the test panel, i.e. the end nearer the ground in each case, during the application of the lacquer and possibly during the drying of the lacquer also. This procedure results in correlation diagrams which are particularly meaningful and differentiating. Many of the optical measurements are made using measuring instruments which emit an illuminating beam and make the measurement on the reflected beam, for example. These instruments therefore have a direction of illumination from which illumination is effected and a direction of observation (measuring direction) which is opposite thereto. In the aforementioned preferred embodiment, it is particularly preferred that the direction of illumination and/or observation, despite the angle of illumination and/or observation which is selected for the measurement, extends on the test panel in the direction of or 180 degrees opposite to an axis of the test panel. The axis which is preferably selected for this purpose is that which, during the application and/or drying of the lacquer coat applied as a wedge or of that lacquer coat applied as a wedge which has the major influence on the corresponding optical measurement, preferably during the application and possibly the drying of the lacquer of this coat, ran from top to bottom on a test panel situated outside the horizontal and which was preferably situated in the vertical. The selection of the lacquer coat from which the major influence on the corresponding measurement stems is clear to one skilled in the ar, or can easily be determined by him by means of experiments. Whether it is preferable to illuminate in the direction of the axis or opposite to the axis depends on the type of lacquer to be tested.

The method according to the invention can also be used in the field of lacquer and binder vehicle development. For example, the influence of the lacquer composition on the visual effect of a single- or multi-layer coating which is obtained whilst adhering to defined conditions of application and drying can be determined. For example, the visual effect of a lacquered surface may depend on the type and quantitative proportion of the binder vehicles in the lacquers, on the type and amount of volatile substances such as solvents for example, on the type and amount of additives, and on the type and amount of pigments and extenders. The method according to the invention can also be successfully used in the styling phase, e.g. for the formulation of new, previously unknown (effect) colour shades. The stability of lacquers over an extended period of time, optionally under special conditions, for example the shelf life and closed circuit stability thereof or the suitability of lacquers for a fixedly predetermined coating process, can also be successfully investigated using the method according to the invention. If, for example, in the case of lacquers with a good shelf life or good closed circuit stability, there is no change in the effect, colour shade or surface structure of surfaces which are coated with them, even over an extended period of time, the pattern is manifested as one which is unchanged in the corresponding correlation diagrams produced by the method according to the invention.

The method according to the invention can also be used for quality control in lacquer manufacture, for the release of colour shades for example. In this connection, test panels coated with the lacquer to be tested or with the lacquers to be tested are produced under defined conditions and the corresponding correlation diagrams are compared with the control diagrams for agreement, as a release criterion. Differences in the lacquer material can be rapidly and reliably identified and can be corrected by taking suitable action as applied to the manufacturing process. In this connection, it is often not only a difference which is identified by means of the correlation diagram, but also the cause thereof In addition, the method according to the invention can be employed in the development of lacquer coating processes, which includes both the process of lacquer application and the lacquer drying process. For example, by using one and the same lacquer, or the same lacquers in the case of multi-layer coatings, and by keeping all the drying parameters constant, the influence of application parameters on the visual effect of the lacquered surface can be investigated. The application parameters can also be kept constant and the drying parameters can be varied. Examples of variable application parameters include the atmospheric humidity, the temperature, the type and mode of operation of the spraying device, the magnitude of the voltage during electrostatic application, and the type and coat thickness of the other lacquer coats of a multi-layer coating which are not applied as wedges. Examples of variable drying parameters include the aeration conditions such as the aeration temperature and duration, the temperature/time heat-up curve of the drying oven, the drying temperature or object temperature as such, the stoving duration and the atmospheric humidity. The method according to the invention is preferably conducted so that only one application or drying parameter is varied, whilst the other application or drying parameters are held constant. The correlation diagram or correlation diagrams obtained by the method according to the invention each represent the influence of the application and/or drying parameters on the visual effect of a lacquered surface.

For example, the optimum processing window of defined lacquers as regards atmospheric humidity and temperature, in which the visual impression and thus the correlation diagrams obtained by the method according to the invention are constant, can be determined for the application of these lacquers, i.e. it is possible to define a reliable processing range for given lacquers.

In addition, in the case of two lacquer coats applied as wedges for example, one or more ranges for lacquer coat combinations such as these of the two coats which are applied as wedges can be determined in which the visual impression of the multi-layer coated surface corresponds to defined specifications. On a diagram on which the coat thickness of one coat applied as a wedge is plotted against the coat thickness of the second coat applied as a wedge, ranges of this type can be made recognisable as a false-colour representation, for example.

Accordingly, the method according to the invention can also successfully be used for the monitoring of coating processes, which includes both the monitoring of the lacquer application and of the drying of the lacquer. For example, if it is ascertained that the lacquer material which is used corresponds to the specifications (which can also be checked by means of the method according to the invention, as mentioned above), differences from the prescribed coating process (such as non-compliance with prescribed application and/or drying parameters, for example) can rapidly be identified and corrected by the application of the method according to the invention. In this situation also, the correlation diagrams often enable not only the difference as such to be identified, but also enable the causes thereof to be identified.

One value of the method according to the invention results in particular from the possibility of studying the interaction between the coating process and the lacquer formulation. It may be desirable, for example, to produce substrates with the same visual impressions in different coating installations comprising different, fixedly predetermined application and/or drying parameters. Thus, for example, by producing the appropriate correlation diagram or correlation diagrams by the method according to the invention, a suitable formulation of additives for the lacquer can be found, which in principle enables the same lacquer to be used in each case and to adapt this lacquer to the particular conditions of different coating installations by means of the appropriate additives in each case. It thus becomes possible for lacquered parts to have the same visual effect in different coating installations, which is reflected in an identical pattern on the respective correlation diagram.

Examples of surface phenomena which can be determined and characterised by means of the procedure according to the invention are given below.

The method according to the invention can advantageously be used for the determination and characterisation of the microstructure, of the wetting behaviour, of the flow, of the run-off tendency, of the etching behaviour and of the orange peel effect, using methods of determining the long wave and/or short wave proportion of the surface structure of lacquered surfaces, particularly by using the aforementioned Wave-scan® measuring instrument.

Moreover, by using calorimetric methods, particularly by determining brightness, the method according to the invention can advantageously be utilised for the determination and characterisation of hiding power, colour shade, brightness flop, colour flop, fogging and spray mist absorption, and of etching effects, and can be utilised, particularly when using base lacquer/clear lacquer double-layer coatings which are produced using effect base lacquers, for determining and characterising run-off phenomena in the effect base lacquer.

The method according to the invention is preferably conducted in an automated manner. For example, the measuring instrument or a plurality of different measuring instruments simultaneously, for example a measuring instrument for gloss measurement, a measuring instrument for determining the surface structure and a measuring instrument for determining brightness, can be guided simultaneously by an automatically operating moving device over the lacquered test panel in accordance with the desired measuring grid. This can be accomplished using a customary X,Y measuring table which is known in the art, for example. The value pairs or value triples formed from measured values and the thicknesses of the wedge-shaped lacquered coat or wedge-shaped lacquered coats associated therewith can be stored, for example, in an attached computer, e.g. a personal computer, and can subsequently printed out as one or more correlation diagrams. For example, this print-out can be produced in the form of a correlation diagram as a two-dimensional representation, or in the case of two lacquer coats in the form of gradients as a three-dimensional representation (a spatial representation of all the optical data points as a function of the two coat thicknesses), or may preferably be produced in the form of a family of correlation diagrams (a plurality of representations comprising the corresponding subset of the optical data points as a function of the coat thickness of one lacquer coat at a constant coat thickness of the second lacquer coat in each case, or vice versa). For example, a spatial representation can be produced of all the optical data points as a function of the base lacquer coat thickness and of the clear lacquer coat thickness of a base lacquer/clear lacquer double-layer coating, or a family of correlation diagrams can be obtained which each depict the relevant part of the optical data points as a function of the base lacquer coat thickness at a constant clear lacquer coat thickness in each case, or vice versa, i.e. the relevant part of the optical data points is represented in each case as a function of the clear lacquer coat thickness at a base lacquer coat thickness which is constant in each case, e.g. for the purpose of performing a night-time measuring operation which is independent of an operator the X,Y measuring table can be coupled to an automatic sample changer in which a plurality of test panels are stacked, with the latter being fed on to the X,Y measuring table in succession for measurement.

Thus the present invention also relates to an apparatus for determining the visual effect of lacquer coatings applied to test panels, comprising a measuring table for the interchangeable placement of test panels, which is characterised in that a holder for measuring instruments intended for the optical assessment and for measuring the coat thickness of lacquer coatings is mounted above the measuring table so that it can travel both in the longitudinal direction (Y axis) and in the transverse direction (X axis) of the measuring table. In this apparatus, the holder is preferably mounted so that it can travel in steps. The holder can be disposed on a travelling bridge mounted on the measuring table.

The bridge can be supported on rails running in the longitudinal direction (Y axis) of the measuring table. The holder can comprise a carriage which is suspended on the crosspiece of the bridge so that it can travel in the transverse direction (X axis) of the measuring table. The carriage preferably comprises holding devices, which are adjustable vertically in relation to the measuring table, for the measuring instruments. In order to carry out the method according to the invention, the bridge and the carriage can be provided with a controller for stopping the bridge and/or carriage at predetermined or arbitrary points.

DETAILED DESCRIPTION OF THE PREFERRED EMBODIMENTS

Figure 1:
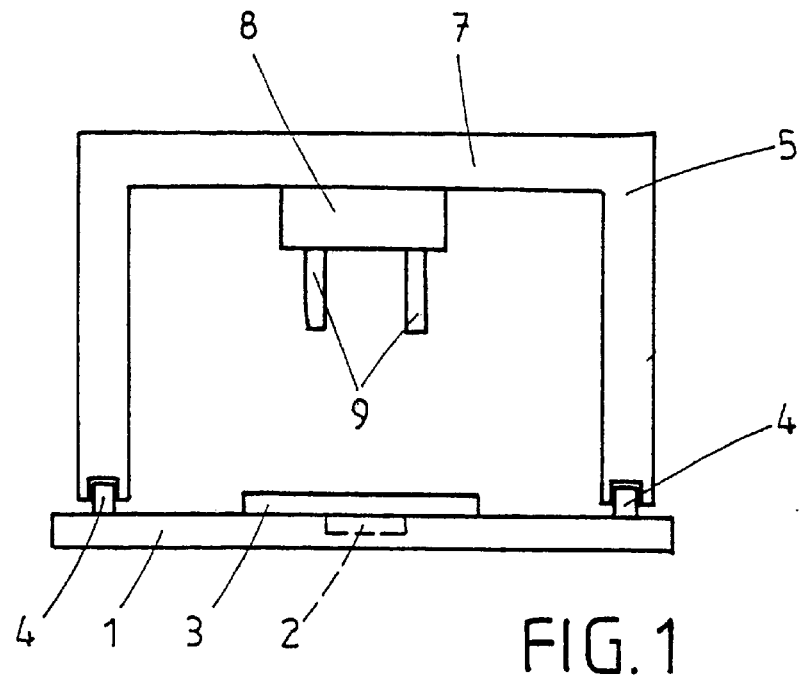
FIG. 1 is a side view of an example of an embodiment of the apparatus according to the invention.
Figure 2:
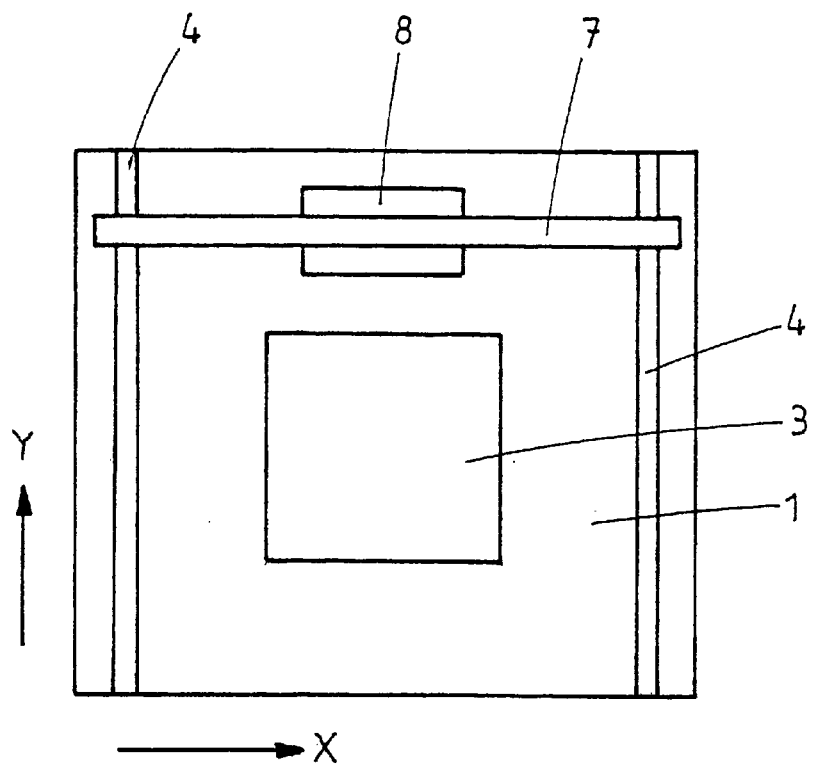
FIG. 2 is a plan view of an example of an embodiment of the apparatus according to the invention.

In the Figures, 1 denotes the measuring table, which is preferably of rectangular or square construction. This measuring table has a mounting 2 for one or more lacquered panels 3 to be assessed, which are laid flat. A bridge 5, which is displaceable in the longitudinal direction (Y axis) of the measuring table, via rails 4 for example, is constructed on the measuring table. This bridge has a crosspiece 7 which is constructed in the transverse direction (X axis) of the measuring table. This crosspiece 7 may be constructed in the form of a rail on which a travelling carriage 8 is suspended. The carriage comprises one or more holding devices 9, which can be adjusted vertically in relation to the measuring table, for the optical measuring instruments and for the measuring instruments for measuring coat thickness. Both the bridge 5 and the carriage 8 have a controller for stopping them at predetermined or arbitrary points.

In the apparatus according to the invention, the controllers which move and stop the measuring instruments both in the longitudinal direction (Y axis) and in the transverse direction (X axis) of the measuring table can be directly coupled to a computer, in which the respective readings of the optical measurements and of the coat thickness measurements are also stored. This computer can produce the desired correlation diagram between the coat thickness measurement and the optical measurements which results in the desired "fingerprint" which is characteristic for the assessment of the visual effect of lacquer coatings.

One or more optical measuring instruments, as well as an instrument for coat thickness measurement, can be attached to the holder 9 of the apparatus according to the invention. The apparatus according to the invention is operated so that the holding device is moved to different measuring points distributed over the surface. The apparatus according to the invention is preferably operated so that the holding device is moved in the shape of a grid-like pattern over the test panel. At each grid point to be measured, the apparatus is stopped and the measuring instrument is lowered towards the test panel by means of the holding device. Due to the possibility of approaching predetermined measuring points, both the optical values of interest and the coat thicknesses can be determined for each measuring point. This is carried out in successive steps. At the same time, measuring instruments can be attached so that one or more optical measurements can be made at different points and coat thickness measurements can be made at other different points.

The method according to the invention can be used successfully and constitutes a valuable tool for lacquer development, for quality control in the field of lacquer manufacture and in the development and monitoring of lacquer coating processes. The correlation diagrams obtained enable predictions to be made of the visual effect of a lacquered surface which is produced using defined lacquers whilst adhering to defined application and/or drying conditions. The characteristic form of the correlation diagrams obtained by the method according to the invention enables a trend to be deduced as regards the change in the visual effect of a lacquered surface as a function of the coat thickness of the lacquer coats concerned.

The method according to the invention provides a good correlation with the visual impression of a lacquered surface as the human eye perceives it. It can be carried out efficiently and rapidly with a small amount of lacquer material and with a single test panel.

Figure 3:
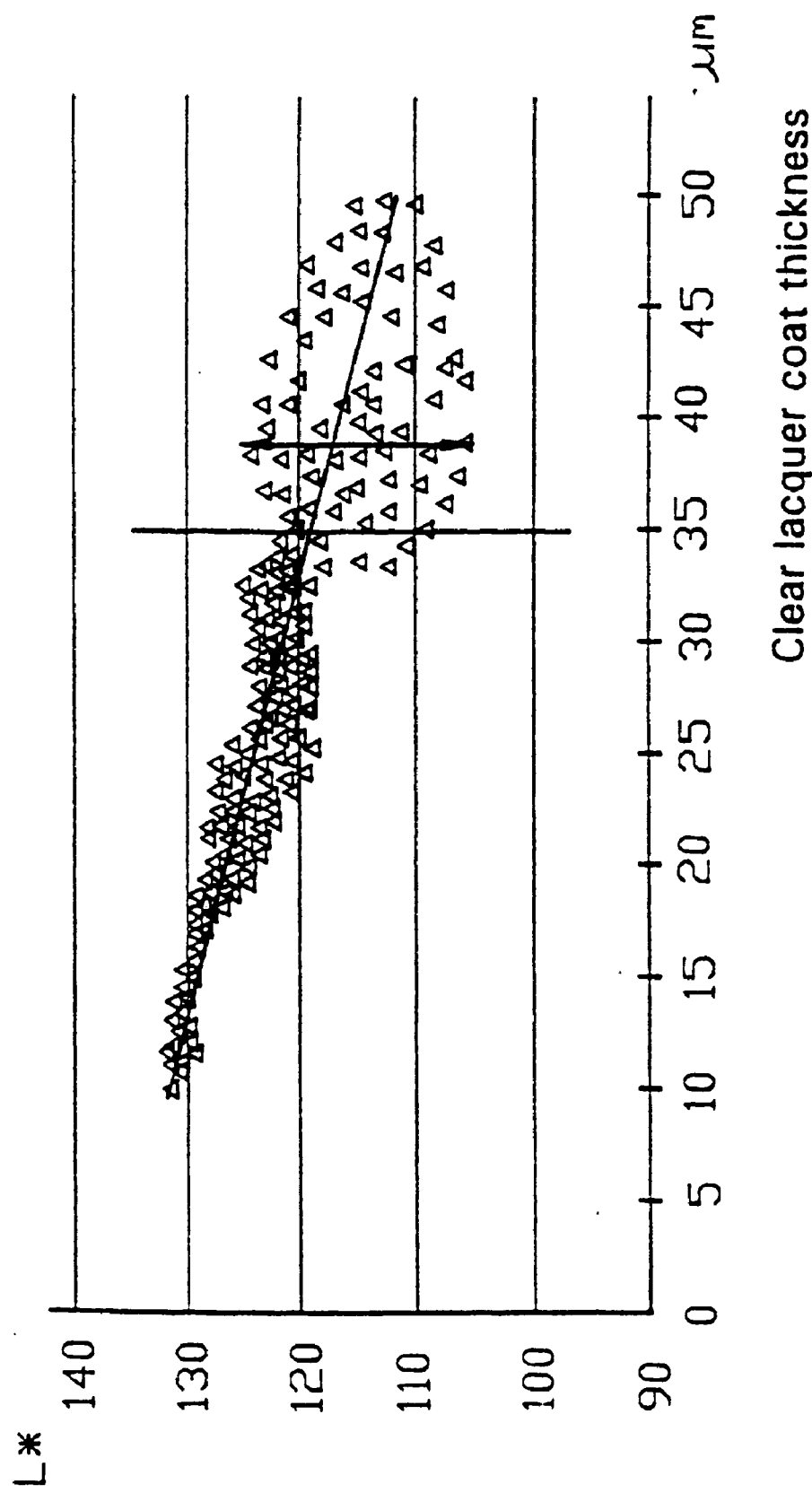
FIG. 3 is a correlation diagram of brightness/thickness for an effect base lacquer/clear base lacquer double layer coating on a substrate.

The accompanying FIG. 3 is an example of a brightness/ clear lacquer coat thickness correlation diagram of an effect base lacquer/clear lacquer double-layer coating. This example clearly illustrates the meaningfulness and value of the method according to the invention. This diagram can be used as a fingerprint and can be compared with the control fingerprint of a specimen lacquer coating, for example.

The fingerprint illustrated in the diagram was obtained by coating a vertically oriented test panel, which had previously been coated with a customary cathodic immersion lacquer coat and a primer surfacer coat, by means of an automatic lacquer spraying machine (as described in EP-B-0 350 891), with a silver-coloured effect base lacquer to give a dry coat thickness of 15 $\mu$m. After aerating for 5 minutes at 80° C., a commercially available two-component clear lacquer with coat thickness gradient of 10 to 50 $\mu$m (greatest clear lacquer thickness at the end of the test panel nearer the ground) was applied by means of the same lacquer automatic lacquer spraying machine and was stoved, jointly with the base lacquer coat, for 30 minutes at 130° C. The brightness of the lacquered surface was measured as a function of the clear lacquer coat thickness, at an angle of illumination of 45 degrees and at an angle of observation of 25 degrees to the gloss reflection, using the Micrometallic® instrument supplied by BYK-Gardner. The directions of illumination and observation were transverse to the clear lacquer wedge.

The following could be read from the correlation diagram, the ordinate of which represents the brightness (L*, according to the CIELAB system) and the abscissa of which represents the clear lacquer coat thickness in $\mu$m: above a clear lacquer coat thickness of about 35 $\mu$m, the base lacquer coat is etched, the brightness value decreases and suddenly exhibits more scatter than in the range of lesser clear lacquer coat thickness. This correlates well with the visual impression, since on observation by eye the occurrence of fogging is observed at a greater clear lacquer coat thickness. In the Figure, the double arrow parallel to the ordinate represents the maximum extent of scatter of the data points.

We claim:

1. A method of determining the visual effect of lacquer coatings in which one, two or three lacquer coatings are applied to the surface of a flat substrate and are dried or hardened, comprising:

applying one or two of the lacquer coats with a wedge-shaped coat thickness gradient, measuring one or more surface properties which influence the visual impression on the lacquered surface thus obtained, at measuring points distributed over the surface, by means of one or more optical methods of measurement, and measuring the respective thickness of the lacquer coat applied in the form of a wedge-shaped gradient or the respective thickness of each one of the two lacquer coats applied in the form of a wedge-shaped gradient.

2. A method according to claim 1, wherein two or more lacquer coats are applied to the surface of a flat substrate and are dried or hardened, wherein two of the lacquer coats are applied with coat thickness gradients disposed at right angles to each other.

3. A method according to claim 1, wherein measurements are made at measuring points which are distributed in the form of a grid-like pattern over part of the area or the whole area of the lacquered surface.

4. A method according to claim 1, wherein application of the lacquer coats is effected on a vertically aligned surface of the substrate, wherein the greatest coat thickness of the gradient is formed in each case at the lower end nearer the ground.

5. A method according to claim 1, wherein the direction of illumination and/or the direction of observation (measuring direction) of the instruments for measuring the lacquered surface is in the direction of or at 180 degrees opposite to the axis of the surface which, on the application of the lacquer coat in the form of a gradient, or in the case of two lacquer coats in the form of a gradient, of that lacquer coat which is of primary interest, ran from top to bottom when the surface was in a vertical position.

6. A method according to claim 1, wherein measurement is made automatically.

7. A method according to claim 1, wherein data points obtained are plotted on one or more correlation diagrams of the coat thickness or coat thicknesses and the optical data point associated therewith in each case.

8. A method according to claim 7, wherein the correlation diagrams are produced automatically via a computer following the respective measurement.

9. A method according to claim 7 wherein a three-dimensional correlation diagram is produced.

10. A method according to claim 7, wherein the correlation diagrams produced are used as a fingerprint for a particular lacquer coating, particularly for comparison with a control fingerprint.

11. A method according to claim 1, wherein gloss, gloss fogging (haze), surface structure, colour location, colour intensity and/or brightness are measured as the surface properties which influence the visual impression.

12. A method according to claim 1, wherein a test panel is used as the surface to be lacquered which has a flat surface.

13. A method according to claim 12, wherein the thickness of the lacquer coat(s) applied in the form of a gradient which is associated with the respective optical measurements is measured by magnetic induction.

14. A method according to claim 1, comprising characterizing microstructure, wetting behaviour, flow, run-off tendency, etching behaviour and/or orange peel effect of lacquers or lacquer coatings using a measuring instruction for assessments of the surface structure.

15. A method according to claim 1, comprising characterizing etching behaviour, run-off tendency, hiding power, colour shade, fogging and/or spray mist absorption of lacquers or lacquer coatings using a colorimetric measuring instrument.

16. A method according to claim 15, comprising characterizing run-off behaviour of effect base lacquers.

17. A method according to claim 1, wherein the method is carried out in the fields of binder vehicle and/or lacquer decelopment, said method comprising testing shelf life and/or closed circuit stability, for quality control and/or development or monitoring of lacquer application and/or of drying or lacquer hardening processes.

18. A method according to claim 1, comprising applying a plurality of coats of different lacquers.

19. An apparatus according to claim 18, wherein the holder (8,9) is disposed on a travelling bridge (5) mounted on the measuring table (1).

20. An apparatus according to claim 19, wherein the bridge (5) is supported on rails running in the longitudinal direction (Y axis) of the measuring table (1) and that the holder (8,9) comprises a carriage (8) which is suspended on the crosspiece (7) of the bridge (5) so that it can travel in the transverse direction (X axis) of the measuring table (1).

21. An apparatus according to claim 20, wherein holding devices (9) for the measuring instruments are disposed on the carriage (8) so that they are adjustable vertically in relation to the measuring table (1).

22. An apparatus according to claim 20, wherein the bridge (5) and the carriage (8) are provided with a controller for stopping the bridge (5) and/or carriage (8) at predetermined or arbitrary points.

23. An apparatus for carrying out the method according to claim 1, with which the visual effect of lacquer coatings applied to test panels (3) is determined, comprising a measuring table (1) for the interchangeable placement of test panels (3), wherein a holder (8,9) for measuring instruments intended for the optical assessment and for measuring the coat thickness of lacquer coatings is mounted above the measuring table (1) so that it can travel both in the longitudinal direction (Y axis) and in the transverse direction (X axis) of the measuring table (1).

24. An apparatus according to claim 23, wherein the holder (8,9) is mounted so that it can travel in steps.

* * * * *